United States Patent
Eimer et al.

(10) Patent No.: US 6,551,059 B2
(45) Date of Patent: Apr. 22, 2003

(54) RADIAL BLOWER, IN PARTICULAR, FOR A BREATHING APPARATUS

(75) Inventors: Georg Eimer, St. Georgen (DE); Wolfgang Fehrenbacher, St. Georgen (DE); Fritz Schmider, Hornberg (DE)

(73) Assignee: Papst-Motoren GmbH & Co. KG, St. Georgen (DE)

( * ) Notice: Subject to any disclaimer, the term of this patent is extended or adjusted under 35 U.S.C. 154(b) by 0 days.

(21) Appl. No.: 09/961,847

(22) Filed: Sep. 24, 2001

(65) Prior Publication Data

US 2002/0057967 A1 May 16, 2002

(30) Foreign Application Priority Data

Sep. 28, 2000 (DE) ...... 200 16 769 U

(51) Int. Cl.⁷ ............ F04D 29/42
(52) U.S. Cl. ......... 415/204; 415/205; 415/206; 416/186 R
(58) Field of Search ........... 415/203, 204, 415/205, 206, 226; 416/185, 214 R, 214 A, 186 R

(56) References Cited

U.S. PATENT DOCUMENTS

| | | | | |
|---|---|---|---|---|
| 4,323,369 A | * | 4/1982 | Monson et al. | 55/1 |
| 4,448,573 A | * | 5/1984 | Franz | 415/206 |
| 5,749,704 A | * | 5/1998 | Jerdee | 415/211.2 |

FOREIGN PATENT DOCUMENTS

DE 197 15 581 2/1999

* cited by examiner

Primary Examiner—Ninh H. Nguyen
(74) Attorney, Agent, or Firm—Gudrun E. Huckett

(57) ABSTRACT

A radial blower, in particular, for a breathing apparatus, has a blower housing with a central, axial intake opening and a radial or approximately tangential outlet opening as well as a motor-driven radial blower wheel arranged axially between the intake opening and the outlet opening. The radial blower wheel has a cover disk at the axial side facing the outlet opening with such a large diameter that between the outer circumference of the cover disk and an inner circumferential surface of the housing a constricted annular flow gap for the medium flowing through the radial blower wheel in the direction toward the outlet opening is formed.

26 Claims, 3 Drawing Sheets

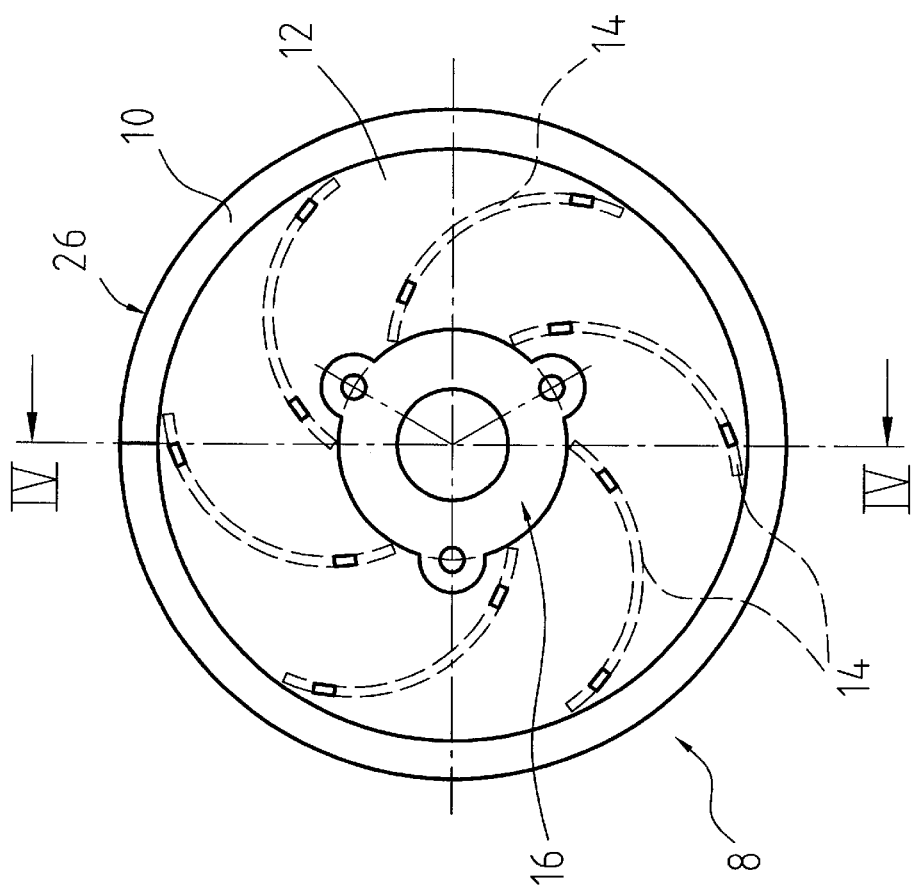
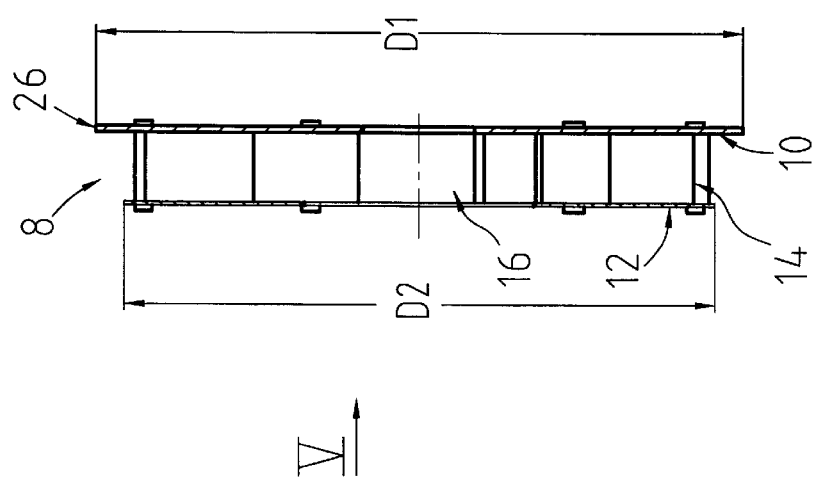

RADIAL BLOWER, IN PARTICULAR, FOR A BREATHING APPARATUS

BACKGROUND OF THE INVENTION

1. Field of the Invention

The invention relates to a radial blower, in particular, for a breathing apparatus, comprising a blower housing with a central, axial intake opening and a radial or approximately tangential outlet opening as well as a motor-driven radial blower wheel arranged axially between the intake opening and the outlet opening and having a central inflow area neighboring the intake opening, wherein, in particular, the intake opening has arranged upstream thereof an intake spiral ("intake air snail") at the exterior housing side such that a medium flows radially or approximately tangentially into a spiral channel and flows from there axially into the central intake opening.

2. Description of the Related Art

DE 197 15 581 C1 and the parallel EP 0 872 643 A2 describe an air supply arrangement for blowers of breathing apparatus, for the treatment of sleep apnea, for example, wherein, with interposition of the blower, an air supply channel is connected to an air outlet. In this connection, the intake spiral is provided for reducing noises generated by the air flow. The known intake spiral is characterized in that the spirally shaped air supply channel is divided into at least two partial channels. The thus resulting partial channels end directly in the vicinity of the central intake opening so that the incoming air reaches directly, i.e., substantially radially, the intake area of the blower wheel and impacts in this area on the inner ends of the blower wheel vanes. The air flows then through the blower wheel radially outwardly and subsequently axially in the direction of the outlet opening.

SUMMARY OF THE INVENTION

The present invention has the object to still further reduce the noise emission for such a radial blower.

The first solution according to the invention resides in that the radial blower wheel has at its axial side facing the outlet opening a cover disk with such a large diameter that between the outer circumference of the cover disk and an inner circumferential surface of the housing a constricted annular flow gap is formed for the medium flowing first radially through the radial blower wheel and then axially in the direction of the outlet opening. In this connection, it is particularly advantageous when the flow gap has an annular flow cross-section which is within a range from smaller than up to maximally 60% greater than the flow cross-section of the outlet opening.

It was found that with this feature according to the invention a distinct noise reduction is obtained. As a result of the constricted flow gap, a calming chamber is formed that encloses the blower wheel and is shaped as an annular chamber in which the medium flowing radially out of the blower wheel is first calmed and then guided via the constricted flow gap in the direction of the outflow chamber provided with the outlet opening and also shaped as an annular chamber.

A second solution according to the invention concerns the area of the intake spiral and resides in that the spiral channel is limited by a corresponding spirally shaped channel wall which, in the vicinity of the central intake opening, ends such that any imaginary tangent placed on the channel wall—in particular, also on its inner end—is positioned outside of the intake opening and the intake area of the blower wheel, or is positioned at most tangentially thereto. In this connection, the intake area of the blower wheel is formed by the radially inwardly positioned ends of the radial vanes wherein these inner ends of the radial vanes are positioned on a circle whose diameter is at least identical to, preferably however slightly greater than, the diameter of the intake opening.

This measure according to the invention is based on the recognition that by providing a lateral air supply according to the prior art (necessary because of the required very flat configuration) results in audible noises because the air flow coming from the intake spiral and entering the central intake area impacts directly approximately radially on the inner ends of the radial vanes and thus causes distinct noises. This can be described as the air flow "sees the inner ends of the vanes". According to the invention, the spiral channel is instead configured such that the air flow will lay itself substantially tangentially against the central opening toward the blower wheel so that the air flow does not impact directly on the radial vanes but instead has a soft transition. This means that the air, coming from the intake spiral, practically "sneaks" noiselessly tangentially into the central intake opening and into the intake area.

The two measures according to the invention can be employed, as desired, alternatively, but with special advantage in combination with one another so that in a concrete realization of the invention a noise level was obtained which was approximately 13 $dB_A$ lower in comparison to a known blower, wherein this improvement is distributed possibly approximately half and half onto the two noise reduction measures according to the invention.

It should be noted that the measures according to the invention are suitable primarily for blowers with a relatively high pressure increase and small volume flow because for this configuration they provide the best sound reduction effect. For this purpose, a working point is selected on the blower characteristic line where for the rated volume flow a relatively small volume flow and a relatively high pressure are present. The rated volume flow and a free blowing volume flow then have a ratio of approximately 1:12 to 1:6, corresponding to approximately 8 to 16%. In an advantageous embodiment, the rated volume flow can be, for example, 50 l/min and the free-blowing volume flow can be 400 l/min resulting in a ratio of 1:8, corresponding to 12.5%.

BRIEF DESCRIPTION OF THE DRAWING

By means of a preferred embodiment illustrated in the drawing the invention will be explained in more detail in the following. It is shown in:

FIG. 4 a reduced scale sectional illustration showing only the radial blower wheel in analogy to FIG. 1 (section in the plane IV according to FIG. 5); and FIG. 5 a plan view onto the intake side of the blower wheel in the direction of arrow V according to FIG. 4.

DESCRIPTION OF THE PREFERRED EMBODIMENTS

Figure 1:
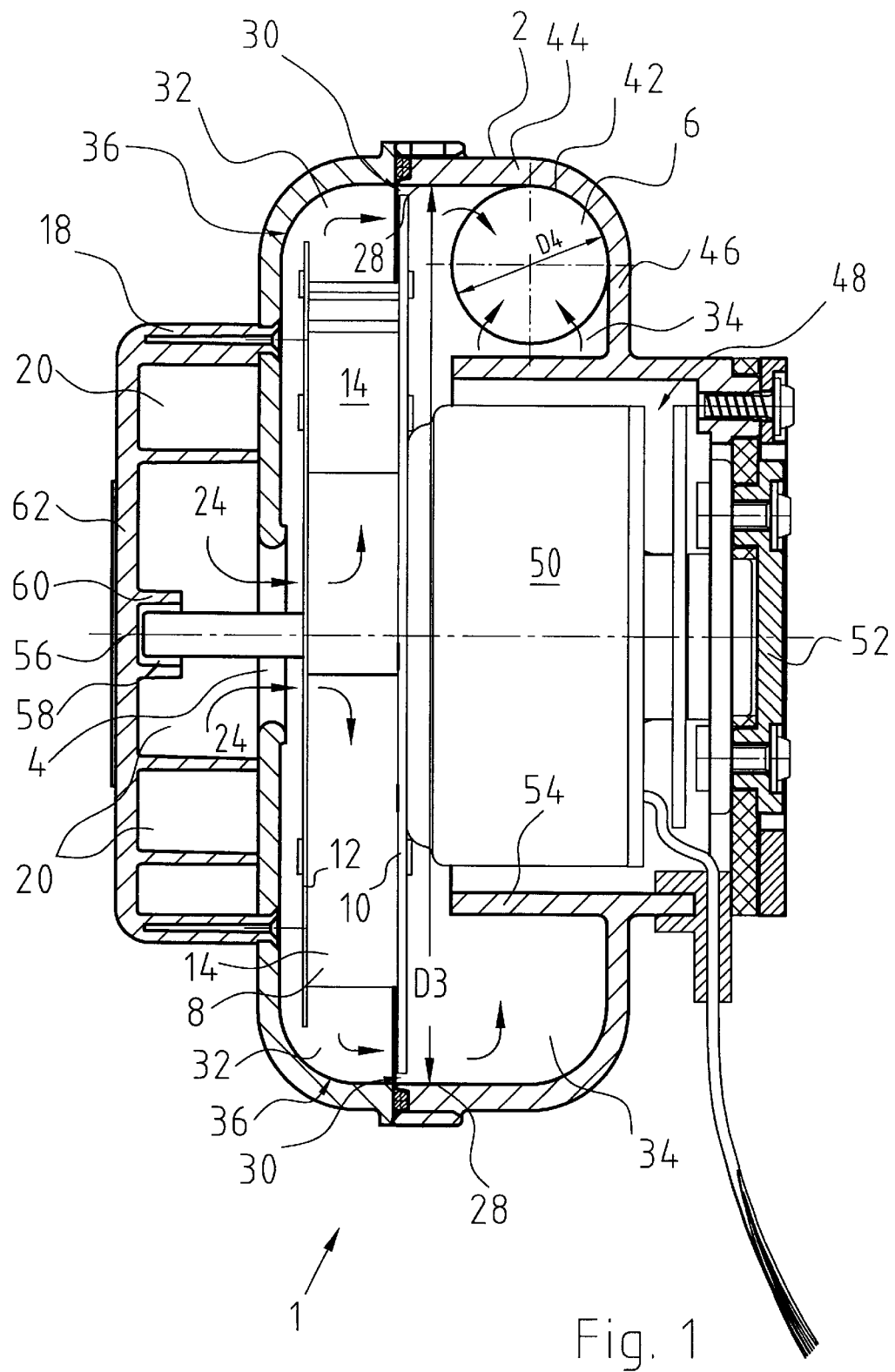
FIG. 1 an axial section of a radial blower according to the invention.

In the different Figures of the drawing the same parts are always identified with the same reference numerals and therefore must be described generally only once.

As can be seen in FIG. 1, a radial blower 1 according to the invention has a blower housing 2 with a central, axial intake opening 4 and a radial or approximately tangential outlet opening 6 arranged displaced in the axial direction relative to the former. Within the blower housing 2 a radial blower wheel 8 is arranged axially between the intake opening 4 and the outlet opening 6 (compare in this connection also FIGS. 4 and 5).

The blower wheel 8 is comprised of a first cover disk 10 at the outlet side, a second cover disk 12 at the intake side, as well as radial vanes 14 arranged between the cover disks 10, 12. According to FIG. 5, the vanes 14 are, depending on the direction of rotation, forwardly, in particular however, rearwardly curved. The radial vanes 14 define with their radial inner ends a central intake area 16 of the blower wheel 8 which is positioned directly adjacent within the area of the intake opening 4.

Preferably, the intake opening 4 has arranged upstream thereof an intake spiral 18 at the exterior of the housing such that the respective medium, in particular, air, flows radially or approximately tangentially into a spiral channel 20 (compare in this connection arrow 22 in FIG. 3) and flows out of it approximately axially into the central intake opening 4 (arrow 24 in FIG. 1). As is known in the art, the intake spiral 18 serves for noise reduction of the intake noises.

As can be taken moreover from FIG. 1, according to the invention the first cover disk 10 at the outlet side has such a large diameter D1 (see FIG. 4) that between the outer circumference 26 of the cover disk 10 and an inner circumferential surface 28 of the housing a constricted annular flow gap 34 is provided for the medium first flowing radially through the blower wheel 8 and then axially in the direction toward the outlet opening 6. By means of this flow gap 30, a calming chamber 32 is formed which encloses the blower wheel 8 circumferentially and in which the medium exiting radially from the blower wheel 8 is calmed to then flow via the flow gap 30 according to the invention axially in the direction of an outflow chamber 34 comprising the outlet opening 6. The flow gap 30 has an annular flow cross-section $A_R$ which is in a range of approximately identical to, or even somewhat smaller than, up to maximally approximately 60% greater than the flow cross-section $A_A$ of the outlet opening 6. The following thus applies: $A_R \leq A_A$ up to $A_R$=appr. $1.6 \times A_A$.

The diameter D1 of the first cover disk 10 forming the constricted flow gap 30 is preferably greater than the diameter D2 of the second cover disk 12 at the intake side (see FIG. 4). Accordingly, the housing 2 can advantageously have a concavely curved—viewed in axial section; see FIG. 1—inner surface 36 in the area circumferentially enclosing the blower wheel 8 such that the air exiting radially from the blower wheel 8 is guided by the concave inner surface 36 in a way that is beneficial with regard to flow in the direction toward the constricted flow gap 30.

In a concrete configuration of the blower according to the invention the following dimensions are present:

| | |
|---|---|
| outer diameter D1 of the first cover disk 10: | 100.6 mm |
| outer diameter D2 of the second cover disk 12: | 90.9 mm |
| inner diameter D3 of the housing in the area of the flow gap 30 or the inner circumferential surface 28: | 103.0 mm |
| inner diameter D4 of the outlet opening 6 (FIG. 1): | 18.0 mm |

In this connection, the radial vanes 14 are positioned with their outer ends on a circle with a diameter of 89.0 mm.

Based on these dimensions, which are provided only as an example, a ratio of the cross-sectional surfaces outlet opening 6 to flow gap 30 of approximately 2:3 results. Accordingly, the flow cross-section $A_R$ of the flow gap 30 is approximately 50% greater than the flow cross-section $A_A$ of the outlet opening 6; therefore the following applies: $A_R = 1.5 \times A_A$.

According to FIG. 1, the outlet opening 6 is radially almost completely covered by an axial projection of the first cover disk 10. The air which flows through the flow gap 30 is distributed therefore first, while experiencing a calming action, within the outlet chamber 34 and then flows in the direction of the arrows illustrated in FIG. 1 into the outlet opening 6.

Figure 3:
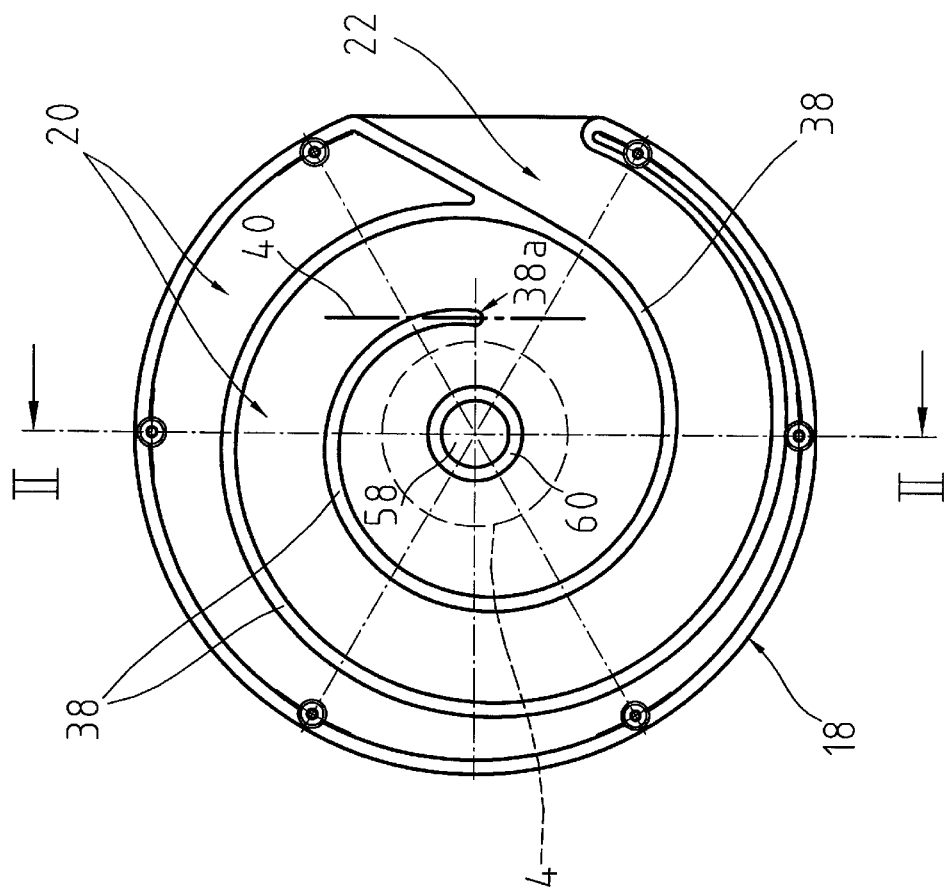
FIG. 3 a plan view onto the inner side of the intake spiral in the direction of arrow III according to FIG. 2.
Figure 2:
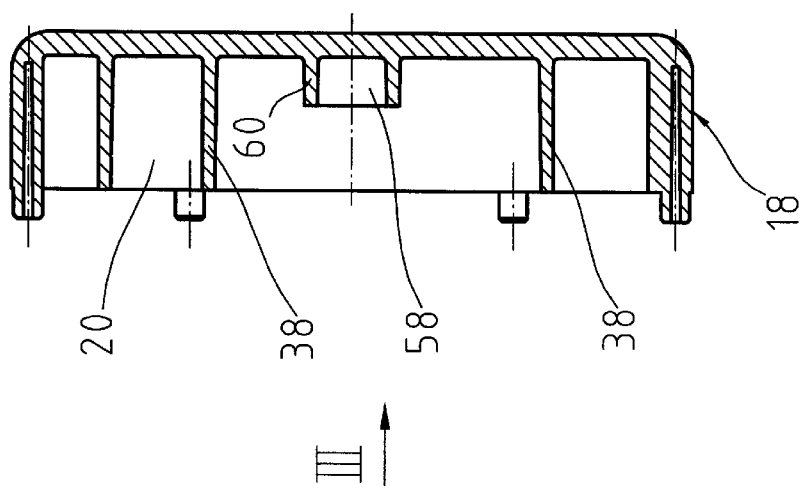
FIG. 2 a separate sectional view analog to FIG. 1 showing only the intake spiral.

Based on FIG. 3 a further aspect according to the invention is to be described. Accordingly, the spiral channel 20 is delimited by a corresponding spirally shaped channel wall 38 which ends in the vicinity of the central intake opening 4, illustrated in FIG. 3 in dashed lines, such that any imaginary tangent (compare, for example, the tangent 40 in FIG. 3) placed on the channel wall 38—in particular also on its end 38a—is positioned outside of the intake opening 4 and the intake area 16 of the blower wheel 8, or is at most positioned tangentially thereto. With this configuration according to the invention, it is prevented that the air flowing from the spiral channel 20 into the intake opening 4 impacts directly onto the inner ends of the radial vanes 14. Accordingly, the corresponding noises are also advantageously prevented in that the air coming from the intake spiral 18 practically "sneaks" noiselessly into the central intake opening 4 and into the intake area 16 of the blower wheel 8. In this way, in the area of the intake opening 4 an air flow is generated which rotates like a vortex, which is especially beneficial for the transition into the radial flow through the blower wheel 8. Moreover, it is advantageous in this connection when the rotational direction of the blower wheel 8 coincides with the imparted angular momentum produced by the spiral channel 20. In this connection, the radial inner ends of the radial vanes 14 which form the intake area 16 are positioned on a circle whose diameter is at least identical to, preferably however approximately somewhat greater than, the diameter of the intake opening 4. Accordingly, a transition from the intake spiral 18 to the blower wheel 8 is achieved which is beneficial with regard to flow and therefore has a low noise level.

The outer ends of the radial vanes 14 of the blower wheel 8 are positioned on a circle whose diameter is approximately identical to the diameter D2 of the second cover disk 12 at the intake side. Accordingly, the radial vanes 14 advantageously leave open the above explained calming chamber 32.

As can be seen in FIG. 1, the outlet opening 6 adjoins preferably directly the inner housing surface 42, concavely curved similar to the inner surface 36, in the area of the transition between a circumferential wall 44 and a radial end face wall 46 of the housing. This is also very beneficial with regard to flow.

Moreover, FIG. 1 shows that the blower housing 2 provides a receiving chamber 48 for an electric motor 50 at a side opposite the intake opening 4 and the intake spiral 18. The electric motor 50 is secured within the receiving chamber 48 by a motor flange 52 which functions at the same time as the closure lid. Moreover, the receiving chamber 48 is also limited within the blower housing 2 by an annular wall 54 which extend in the axial direction of the blower wheel 8 and is thus enclosed annularly, respectively, circumferentially by the outlet chamber 34. In this connection, it is moreover advantageous when the rotor has a shaft portion 56 projecting past the radial blower wheel 8 in the axial direction which with its free end is guided in a bearing receptacle 58. Preferably, the bearing receptacle 58 is a component of the intake spiral 18, for example, by being formed by a unitary to annular projection 60 of a radial end wall 62 of the spiral housing. With this advantageous feature, the blower wheel 8 is guided against impact loading, which is particularly important because of the relatively narrow flow gap 30, in order to avoid grinding noises of the blower wheel 8 or of the cover disc 10 at the inner circumferential surface 28 when impact loading occurs. For this purpose, the guiding play of the shaft portion 56 within the bearing receptacle 58 is in any case smaller than the flow gap 30.

With the described measures according to the invention, a distinct reduction of the flow noises is achieved. This holds true, in particular, also in the case of a return air flow, for example, in the case of a breathing apparatus, when exhaling causes the air flow to return. By means of the invention, such a return flow is, in particular, also calmed so that the noises are significantly reduced. In this connection, the features according to the invention are suitable primarily for such blowers in which the rated volume flow and the free-blowing volume flow have a ratio of approximately 1:12 up to 1:6, corresponding approximately to 8 to 16%.

The invention is not limited to the illustrated and described embodiments but includes also embodiments functioning in the same way within the meaning of the invention. Moreover, the invention is also not to be understood to be limited at present to the feature combinations defined in the independent claims but can also be defined by any desired other combination of certain features of all individual features disclosed. This means that basically practically each individual feature of the claims can be omitted or replaced by at least one individual feature disclosed at a different location within the application.

What is claimed is:

1. A radial blower (1) comprising:
   a blower housing (2) having a central, axial intake opening (4) and at least one of a radial outlet opening and a substantially tangential outlet opening (6);
   a motor-driven radial blower wheel (8) arranged in the blower housing (2) axially between the intake opening (4) and the at least one of a radial outlet opening and a substantially tangential outlet opening (6), wherein the radial blower wheel (8) comprises a first cover disk (10) arranged at an axial side of the radial blower wheel (8) facing the at least one of a radial outlet opening and a substantially tangential outlet opening (6);
   wherein the first cover disk (10) has such a diameter (D1) that a constricted annular flow gap (30) for a medium, flowing through the radial blower wheel (8) from the intake opening (4) in the direction toward the at least one of a radial outlet opening and a substantially tangential outlet opening (6), is formed between an outer circumference (26) of the first cover disk (10) and an inner circumferential surface (28) of the blower housing (2);
   wherein the flow gap (30) has an annular flow cross-section ($A_R$) which has a range of smaller than up to maximally 60% greater than the flow cross-section ($A_A$) of the at least one of a radial outlet opening and a substantially tangential outlet opening (6).

2. The radial blower according to claim 1, further comprising an intake spiral (18) having a spiral channel (20) connected to the blower housing (2) on an exterior housing side having arranged therein the intake opening (4) so that the intake spiral (18) is positioned upstream of the intake opening (4) and the medium flows radially or approximately tangentially (22) into the spiral channel (20) of the intake spiral (18) and from the spiral channel (20) axially into the intake opening (4) and into a central intake area (16) of the blower wheel (8).

3. The radial blower according to claim 2, wherein the spiral channel (20) is delimited by a spirally shaped channel wall (38) which ends in the vicinity of the intake opening (4) such that any imaginary tangent (40) placed on the channel wall (38) is positioned outside of the intake opening (4) and the intake area (16) of the blower wheel (8) or is at most positioned tangentially thereto.

4. The radial blower according to claim 2, further comprising an electric motor (50) having a rotor, wherein the blower wheel (8) is connected to the rotor of the electric motor (50).

5. The radial blower according to claim 4, wherein the electric motor (50) is preferably mounted in the blower housing (2).

6. The radial blower according to claim 4, wherein the rotor has a shaft portion (56) extending through the blower wheel (8) and projecting from a side of the blower wheel (8) remote from the electric motor (50), wherein the intake spiral (18) has a bearing receptacle (58) and wherein the rotor has a free end guided in the bearing receptacle (58).

7. The radial blower according to claim 1, wherein the blower wheel (8) has a second cover disk (12) facing the intake opening (4) and wherein the second cover disk (12) has a diameter (D2) which is smaller than the diameter (D1) of the first cover disk (10).

8. The radial blower according to claim 7, wherein the blower wheel (8) has radial vanes (14) having radial outer ends positioned on a circle, wherein a diameter of the circle of the radial outer ends matches approximately the diameter (D2) of the second cover disk (12).

9. The radial blower according to claim 1, wherein the blower housing (2) has a concave inner surface (36) in an area circumferentially surrounding the blower wheel (8) which concave inner surface (36) is formed such that the medium, exiting radially from the blower wheel (8), is guided by the concave inner surface (36) in a direction toward the constricted flow gap (30) in a flow-enhancing way.

10. The radial blower according to claim 1, wherein the blower wheel (8) has radial vanes (14) having radially inner ends forming an intake area (16) of the blower wheel (8) and being positioned on a circle having a diameter that is at least identical to or greater than a diameter of the intake opening (4).

11. The radial blower according to claim 1, wherein the housing (2) has a circumferential wall (44), a radial end face wall (46) opposite the intake opening (4), and an inner concavely curved housing surface (42) forming a transition between the circumferential wall (44) and the radial end face wall (46), wherein the at least one of a radial outlet opening and a substantially tangential outlet opening (6) adjoins directly the inner concavely curved housing surface (42).

12. The radial blower according to claim 1, wherein the radial blower has a blower working point located in an area of the blower characteristic line where for the rated volume flow a relatively small volume flow and a relatively high pressure are present.

13. The radial blower according to claim 12, wherein the rated volume flow and a free-blowing volume flow have a ratio of approximately 1:12 to 1:6, corresponding approximately to 8 to 16%.

14. A radial blower (1) comprising:
a blower housing (2) having a central, axial intake opening (4) and at least one of a radial outlet opening and a substantially tangential outlet opening (6);
a radial blower wheel (8) having a central intake area (16) and being arranged within the blower housing (2) such that the central intake area (16) is arranged adjacent to the intake opening (4);
an intake spiral (18) having a spiral channel (20) connected to the blower housing (2) on an exterior housing side having arranged therein the intake opening (4) so that the intake spiral (18) is positioned upstream of the intake opening (4) and a medium flows radially or approximately tangentially (22) into the spiral channel (20) of the intake spiral (18) and from the spiral channel (20) axially into the intake opening (4);
wherein the spiral channel (20) is delimited by a spirally shaped channel wall (38) which ends in the vicinity of the intake opening (4) such that any imaginary tangent (40) placed on the channel wall (38) is positioned outside of the intake opening (4) and the intake area (16) of the blower wheel(S) or is at most positioned tangentially thereto.

15. The radial blower according to claim 14, wherein the radial blower wheel (6) is arranged axially between the intake opening (4) and the outlet opening (6) of the blower housing (2), wherein the radial blower wheel (8) comprises a first cover disk (10) arranged at an axial side of the radial blower wheel (8) facing the outlet opening (6), and wherein the first cover disk (10) has such a diameter (D1) that a constricted annular flow gap (30) for the medium, flowing through the radial blower wheel (8) from the intake opening (4) in the direction toward the at least one of a radial outlet opening and a substantially tangential outlet opening (6), is formed between an outer circumference (26) of the first cover disk (10) and an inner circumferential surface (28) of the blower housing (2).

16. The radial blower according to claim 15, wherein the flow gap (30) has an annular flow cross-section ($A_R$) which has a range of smaller than up to maximally 60% greater than the flow cross-section ($A_A$) of the at least one of a radial outlet opening and a substantially tangential outlet opening (6).

17. The radial blower according to claim 15, wherein the blower wheel (8) has a second cover disk (12) facing the intake opening (4) and wherein the second cover disk (12) has a diameter (D2) which is smaller than the diameter (D1) of the first cover disk (10).

18. The radial blower according to claim 17, wherein the blower wheel (8) has radial vanes (14) having radial outer ends positioned on a circle, wherein a diameter of the circle of the radial outer ends matches approximately the diameter (D2) of the second cover disk (12).

19. The radial blower according to claim 15, wherein the blower housing (2) has a concave inner surface (36) in an area circumferentially surrounding the blower wheel (8) which concave inner surface (36) is formed such that the medium, exiting radially from the blower wheel (8), is guided by the concave inner surface (36) in a direction toward the constricted flow gap (30) in a flow-enhancing way.

20. The radial blower according to claim 14, further comprising an electric motor (50) having a rotor, wherein the blower wheel (8) is connected to the rotor of the electric motor (50).

21. The radial blower according to claim 20, wherein the electric motor (50) is preferably mounted in the blower housing (2).

22. The radial blower according to claim 20, wherein the rotor has a shaft portion (56) extending through the blower wheel (8) and projecting from a side of the blower wheel (8) remote from the electric motor (50), wherein the intake spiral (18) has a bearing receptacle (58) and wherein the rotor has a free end guided in the bearing receptacle (58).

23. The radial blower according to claim 14, wherein the blower wheel (8) has radial vanes (14) having radially inner ends forming the intake area (16) and positioned on a circle having diameter that is at least identical to or greater than a diameter of the intake opening (4).

24. The radial blower according to claim 14, wherein the blower housing (2) has a circumferential wall (44), a radial end face wall (46) opposite the intake opening (4), and an inner concavely curved housing surface (42) forming a transition between the circumferential wall (44) and the radial end face wall (46), wherein the at least one of a radial outlet opening and a substantially tangential outlet opening (6) adjoins directly the inner concavely curved housing surface (42).

25. The radial blower according to claim 14, wherein the radial blower has a blower working point located in an area of the blower characteristic line where for the rated volume flow a relatively small volume flow and a relatively high pressure are present.

26. The radial blower according to claim 25, wherein the rated volume flow and the free-blowing volume flow have a ratio of approximately 1:12 to 1:6, corresponding approximately to 8 to 16%.

* * * * *